US006921667B2

(12) United States Patent
Dervieux et al.

(10) Patent No.: US 6,921,667 B2
(45) Date of Patent: Jul. 26, 2005

(54) METHODS FOR DIRECT DETECTION OF INDIVIDUAL METHOTREXATE METABOLITES

(75) Inventors: Thierry Dervieux, San Diego, CA (US); Russell B. Richerson, Tucson, AZ (US)

(73) Assignee: Prometheus Laboratories, Inc., San Diego, CA (US)

( * ) Notice: Subject to any disclaimer, the term of this patent is extended or adjusted under 35 U.S.C. 154(b) by 76 days.

(21) Appl. No.: 10/384,066

(22) Filed: Mar. 7, 2003

(65) Prior Publication Data

US 2004/0175834 A1 Sep. 9, 2004

(51) Int. Cl.$^7$ .............................................. G01N 33/48
(52) U.S. Cl. ..................... 436/63; 436/106; 436/161; 436/164; 436/171; 436/172; 436/173; 435/2; 435/29
(58) Field of Search ........................... 436/63, 89, 106, 436/161, 164, 171, 172, 173; 435/2, 4, 29

(56) References Cited

PUBLICATIONS

Masson et al. Journal of Clinical Investigation, vol. 97, No. 1, Jan. 1996, pp. 73–80.*
Synold et al. Journal of Clinical Investigation, vol. 94, Nov. 1994, pp. 1996–2001.*
Derivieux et al. Leukemia, vol. 16, 2002, pp. 209–212.*
Dervieux et al. Clinical Chemistry, vol. 49, No. 10, Oct. 2003, pp. 1632–1641.*
Alarcón, "Methotrexate use in rheumatoid arthritis. A clinician's perspective," *Immunopharm.* 47:259–271 (2000).
Angelis–Stoforidis et al., "Methotrexate polyglutamate levels in circulating erythrocytes and polymorphs correlate with clinical efficacy in rheumatoid arthritis," *Clin. Exp. Rheumatology* 17:313–320 (1999).
Anzai et al., "Separation and identification of methotrexate and its metabolites, 7–hydroxymethotrexate and polyglutamates, in human tissues by reversed–phase high–performance liquid chromatography coupled with radioimmunoassay," *J. Chromatogr.* 415:445–449 (1987).
Chaykovsky, "Direct $N^8$–Alkylation of 2,4–Diamino–7, 8–dihydropteridines. Preparation of 7,8–Dihydro–8–methlmethotrexate$^{1}$," *J. Org. Chem.* 40:145–146 (1975).
Dervieux et al., "De novo purine synthesis inhibition and antileukemic effects of mercaptopurine alone or in combination with methotrexate in vivo," *Blood* 100:1240–1247 (2002).
Frei et al., "Clinical studies of dichloromethotrexate (NSC 29630)" *Clin. Pharmacol. Therap.* 6:160–171 (1965).

Galpin et al., "Differences in Polypolyglutamate Synthetase and Dihydrofolate Reductase Expression in Human B–Lineage versus T–Lineage Leukemic Lymphoblasts: Mechanisms for Lineage Differences in Methotrexate Polyglutamylation and Cytotoxicity," *Mol. Pharm.* 52:155–163 (1997).
Imbert et al., "Enzymatic Assay for Methotrexate with a Centrifugal Analyzer (Cobas–Bio),"*Clin. Chem.* 29:1317–1318 (1983).
Jolivet and Chabner, "Intracellular Pharmacokinetics of Methotrexate Polyglutamates in Human Breast Cancer Cells: Selective Retention and Less Dissociable Binding of 4–$NH_2$–10–$CH_3$–Pteroylglutamate$_4$ and 4–$NH_2$–10–$CH_3$–Pteroylglutamate$_5$ To Dihydrofolate Reductase," *J. Clin. Invest.* 72:773–778 (1983).
Kamen, "Folate and Antifolate Pharmacology," *Semin. Oncol.* 24:S18–30 to S18–39 (1997).
Kamen and Winick, "Analysis of Methotrexate Polyglutamate Derivatives in Vivo," *Meth. Enz.* 122:339–346 (1986).
Krakower et al., "Separation and Identification of Subpicomole Amounts of Methotrexate Polyglutamates in Animal and Human Biopsy Material," *Analytical Biochem.* 122:412–416 (1982).
Longo–Sorbello and Bertino, "Current understanding of methotrexate pharmacology and efficacy in acute leukemias. Use of newer antifolates in clinical trials," *Haematolgica* 86:121–127 (2001).
Lucock et al., "Analysis and Biochemistry of Blood Folate," *Biochem. Mol. Med.* 58:93–112 (1996).
McGown et al., "Results with Commercial Radioassay Kits Compared with Microbiological Assay of Folate in Serum and Whole–Blood," *Clin. Chem.* 24:2186–2191 (1978).
Muindi et al., "Specific and sensitive high–performance liquid chromatographic method with fluorescence detection for measurement of lometrexol and its polyglutamates in biologic samples," *J. Chromatogr.* 621:55–64 (1993).
Ndaw et al., "Determination of folates in foods by high––performance liquid chromatography with fluorescence detection after precolumn conversion to 5–methyltetrahydrofolates," *Journal of Chromatography* 928:77–90 (2001).
Pfeiffer and Gregory, "Enzymatic deconjugation of erythrocyte polyglutamyl folates during preparation for folate assay: investigation with reversed–phase liquid chromatography," *Clinical Chemistry* 42:1847–1854 (1996).

(Continued)

Primary Examiner—Maureen M. Wallenhorst
(74) Attorney, Agent, or Firm—Townsend and Townsend and Crew LLP

(57) ABSTRACT

The present invention provides a method for determining a level of a methotrexate polyglutamate (MTXPG) in a cellular extract by resolving at least one MTXPG in a cellular extract obtained from a human undergoing methotrexate therapy; and detecting at least one resolved MTXPG, thereby determining a level of the resolved MTXPG. A method of the invention can be useful, for example, for determining a level of $MTXPG_3$, $MTXPG_4$ or $MTXPG_5$ or for determining a level of each methotrexate polyglutamate species ($MTXPG_1$ to $MTXPG_7$) present in the cellular extract.

77 Claims, 5 Drawing Sheets

OTHER PUBLICATIONS

Rubino, "Separation methods for methotrexate, its structural analogues and metabolites," *J. Chromatog.* 764:217–254 (2001).

Šalamoun and František, "Determination of Methotrexate And Its Metabolites 7–Hydroxymethotrexate and 2,4–Diamino–$N^{10}$–Methylpteroic Acid In Biological Fluids By Liquid Chromatography With Fluorimetric Detection," *Journal of Chromatography* 378:173–181 (1986).

Šalamoun et al., "Column Liquid Chromatography Of Methotrexate And Its Metabolites Using A Post–Column Photochemical Reactor And Fluorescence Detection," *Journal of Chromatography* 419:213–223 (1987).

Schrøder and Heinsvig, "Enzymatic assay for methotrexate in erythrocytes," *Scand. J. Clin. Lab. Invest.* 45:657–659 (1985).

Sczesny et al., "Capillary electophoretic drug monitoring of methotrexate and leucovorin and their metabolites," *J. Chromatogr B. Biomed. Sci. Appl.* 718:177–185 (1998).

Waltham et al., "Capillary electrophoresis of methotrexate polyglutamates and its application in evaluation of gamma–glutamyl hydrolase activity," *J. Chromatorgr B. Biomed. Sci. Appl.* 689:387–392 (1997).

Widemann et al., "Dihydrofolate Reductase Enzyme Inhibition Assay for Plasma Methotrexate Determination Using a 96–Well Microplate Reader," *Clin. Chemistry* 45:223–228 (1999).

Widemann et al., "Pharmacokinetics and Metabolism of the Methotrexate Metabolite 2,4–Diamino–$N^{10}$–methylpteroic Acid," *J. Pharmacol. Exp. Ther.* 294:894–901 (2001).

* cited by examiner

Methotrexate

Methotrexate polyglutamates

METHODS FOR DIRECT DETECTION OF INDIVIDUAL METHOTREXATE METABOLITES

FIELD OF THE INVENTION

This invention relates generally to methods for monitoring drug therapy and, more specifically, to methods for monitoring efficacy and toxicity of methotrexate drug therapy.

BACKGROUND OF THE INVENTION

Folate (folic acid) is a vitamin that is essential for the life-sustaining processes of DNA synthesis, replication and repair. Folate is also important for protein biosynthesis, another process that is central to cell viability. The pteridine compound, methotrexate (MTX), is structurally similar to folate and as a result can bind to the active sites of a number of enzymes that normally use folate as a coenzyme for biosynthesis of purine and pyrimidine nucleotide precursors of DNA and for interconversion of amino acids during protein biosynthesis. Despite its structural similarity to folic acid, methotrexate cannot be used as a cofactor by enzymes that require folate, and instead competes with the folate cofactor for enzyme binding sites, thereby inhibiting protein and DNA biosynthesis and, hence, cell division.

The ability of methotrexate to inhibit cell division has been exploited in the treatment of a number of diseases and conditions that are characterized by rapid or aberrant cell growth. As an example, autoimmune diseases are characterized by an inappropriate immune response directed against normal autologous (self) tissues and are mediated by rapidly replicating T-cells or B-cells. Autoimmune diseases that have been treated with methotrexate include, without limitation, rheumatoid arthritis and other forms of arthritis, psoriasis, multiple sclerosis, the autoimmune stage of diabetes mellitus (juvenile-onset or Type 1 diabetes), autoimmune uveoretinitis, myasthenia gravis, autoimmune thyroiditis, and systemic lupus erythematosus.

Because many malignant cells proliferate more rapidly than normal cells, methotrexate can also be used to selectively impair cancerous cell growth. As a consequence, methotrexate is a widely used anticancer agent, employed, for example, in the treatment of acute lymphocytic leukemia, breast cancer, epidermoid cancers of the head and neck, advanced mycosis fungoides, lung cancer, non-Hodgkins lymphomas, gestational choriocarcinoma, chorioadenoma destruens, and hydatidiform moles.

Despite its therapeutic efficacy for a wide variety of diseases and conditions, treatment with methotrexate can present a risk to the patient. In particular, because methotrexate interferes with processes required for replication and division of normal as well as diseased cells, inappropriately high levels of the drug can lead to destruction of actively proliferating non-target tissues such as bone marrow and intestinal mucosa. Methotrexate has been associated with renal and hepatic toxicity when administered in the "high-dose regimen" that is required for some conditions. In addition, low-dose methotrexate therapy can lead to toxicity and unwanted side-effects in some patients, where the dosage is not appropriate due to individual variability in pharmacokinetic parameters influencing, for example, drug uptake, targeting and clearance. This situation is especially problematic in the treatment of chronic conditions such as rheumatoid arthritis, where methotrexate can be administered over a period of many years.

Because individual differences in pharmacokinetic parameters can be difficult to predict, safe and effective methotrexate treatment strategies require that methotrexate or methotrexate metabolite levels be monitored in patients being treated. A variety of methods have been developed for monitoring methotrexate drug concentrations in plasma including bioassays, immunological detection and chromatographic assays. Such plasma detection methods have been useful for monitoring high dose methotrexate therapy in some clinical applications. However, due to limitations in their sensitivity, these plasma detection methods have not been useful in monitoring low-dose methotrexate therapy, for which intracellular levels of methotrexate metabolites must be assayed.

Methotrexate is metabolized upon uptake by mammalian cells, such that one or more glutamyl moieties are added to methotrexate to yield a mixture of methotrexate polyglutamates (MTXPGs). The number of glutamyl moieties that can be added to MTX generally varies from two to seven. MTXPGs do not readily efflux from cells and thus are able to exert their cytotoxic effects over long periods of time. Levels of intracellular MTXPGs have been shown to be higher in patients that responded to methotrexate therapy as compared to intracellular levels in patients that did not respond. Currently available methods for measuring intracellular methotrexate polyglutamate levels are based on a dihydrofolate reductase enzyme assay in which methotrexate polyglutamate levels are calculated based on their ability to inhibit the dihydrofolate reductase enzyme. However, the extent of enzyme inhibition in these assays is dependent upon the number of glutamyl residues attached to methotrexate, rendering an accurate determination of intracellular methotrexate polyglutamate levels impossible by this method. The variability of dihydrofolate reductase based assays can be further exacerbated in some situations because folates, which are present in different amounts depending upon an individual's response to methotrexate therapy and the amount of folate contributed by diet, also influence the results of the current enzyme assay.

Thus, there exists a need for new methods for determining intracellular levels of methotrexate polyglutamates and for monitoring the efficacy and toxicity of methotrexate therapy including low-dose methotrexate therapy. The present invention satisfies this need and provides related advantages as well.

SUMMARY OF THE INVENTION

The present invention provides a method for determining a level of a methotrexate polyglutamate (MTXPG) in a cellular extract by resolving at least one MTXPG in a cellular extract obtained from a human undergoing methotrexate therapy; and detecting at least one resolved MTXPG, thereby determining a level of the resolved MTXPG. A method of the invention can be useful, for example, for determining a level of $MTXPG_3$, $MTXPG_4$ or $MTXPG_5$, or for determining a level of each methotrexate polyglutamate species ($MTXPG_1$ to $MTXPG_7$) present in the cellular extract.

The present invention also provides a method for determining a level of a methotrexate polyglutamate in a cellular extract by resolving at least one MTXPG in the cellular extract, where the MTXPG contains no more than a natural abundance of radioactive isotopes; and detecting at least one resolved MTXPG, thereby determining a level of the resolved MTXPG, where detection of the resolved MTXPG does not require fractionation of the resolved MTXPG from other MTXPG species. In one embodiment, a method of the invention is used to determine a level of $MTXPG_3$, $MTXPG_4$ or $MTXPG_5$. In another embodiment, a method of the invention is used to determine a level of each $MTXPG_1$ to $MTXPG_7$ species, where detection of $MTXPG_1$ to $MTXPG_7$ does not require fractionation of the $MTXPG_1$ to $MTXPG_7$ species from each other.

Further provided herein is a method for determining a level of a methotrexate polyglutamate in a cellular extract by resolving at least one MTXPG in the cellular extract; irradiating the at least one MTXPG, thereby producing at least one resolved fluorescent MTXPG photolytic product; and detecting the at least one resolved fluorescent MTXPG photolytic product, thereby determining a level of the MTXPG. A method of the invention can be useful, for example, for determining a level of $MTXPG_3$, $MTXPG_4$ or $MTXPG_5$, or for determining a level of each $MTXPG_1$ to $MTXPG_7$ species present in the cellular extract.

Also provided by the invention is a method of optimizing therapeutic efficacy or reducing toxicity associated with methotrexate therapy administered to a human by resolving at least one MTXPG in a cellular extract obtained from the human; detecting at least one resolved MTXPG, thereby determining a level of the resolved MTXPG; and selecting a drug or dosage to be subsequently administered to the human based on the level of the resolved MTXPG. A method of the invention can be useful, for example, for determining a level of $MTXPG_3$, $MTXPG_4$ or $MTXPG_5$, or for determining a level of each $MTXPG_1$ to $MTXPG_7$ species present in the cellular extract. A method of the invention can involve altering a methotrexate dosage subsequently administered to the human, for example, reducing or increasing a methotrexate dosage subsequently administered to the human, or altering a dose of folic acid, or a derivative thereof, subsequently administered to the human.

DETAILED DESCRIPTION OF THE INVENTION

Figure 1:
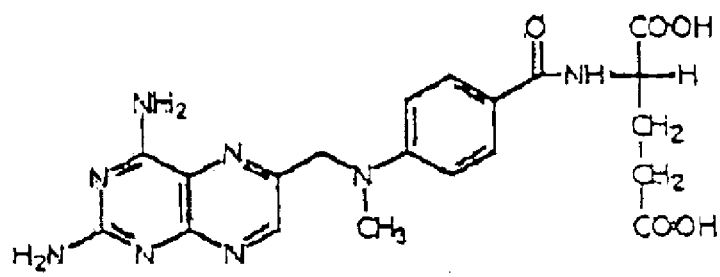
FIG. 1 shows the structures of methotrexate and methotrexate polyglutamates. (A) The chemical structure of methotrexate. (B) The chemical structure for the methotrexate polyglutamates, where n refers to the number of glutamates attached to methotrexate.
Figure 1:
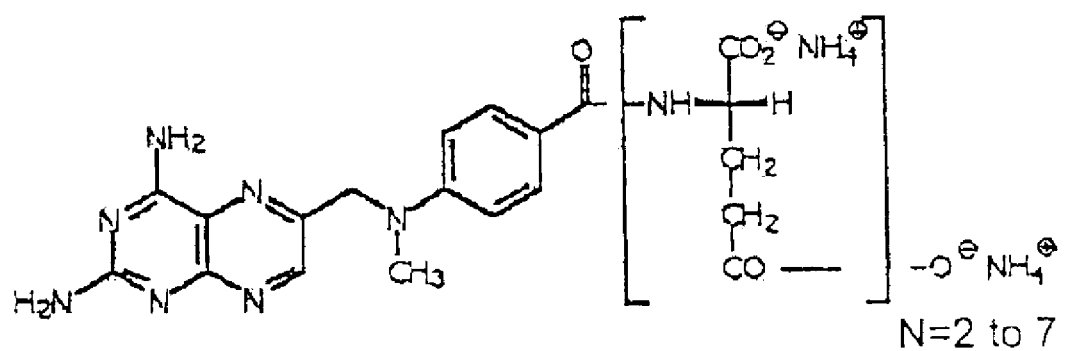

As disclosed herein, a reverse phase liquid chromatographic assay was developed for quantification of individual methotrexate polyglutamate concentrations in red blood cell extracts prepared from individuals undergoing low-dose methotrexate therapy. As disclosed in Example I, the assay includes perchloric acid sample treatment and direct injection of resulting supernatant into an HPLC system composed of a C18 reversed phase column, with ammonium acetate/acetonitrile buffer (pH 6.5) as the mobile phase. In contrast to previously described enzymatic methods for assessing methotrexate metabolites, methotrexate polyglutamates were detected fluorimetricly after post-column photo-oxidation in the presence of hydrogen peroxide. As disclosed in Example I, coefficients of variation for intra-day and inter-day precision were less than 10% for both high and low concentrations of methotrexate polyglutamates. Furthermore, as little as 5 nmol methotrexate polyglutamate per liter packed red blood cells was detected. As further disclosed herein, methotrexate polyglutamate concentrations were determined in red blood cell samples from 14 arthritis patients receiving low dose methotrexate therapy (median drug dose of 16 mg/week).

Unlike older methodologies, the methods of the invention can be used to detect methotrexate polyglutamate metabolites at the fairly low levels at which they occur in patients treated with low-dose methotrexate therapy and can be useful for accurately detecting each of the individual polyglutamates, $MTXPG_1$ to $MTXPG_7$. The methods of the invention further can be conveniently practiced without the need for radiolabeling or for assaying multiple fractions.

Based on the findings described above, the present invention provides a method for determining a level of a methotrexate polyglutamate in a cellular extract by resolving at least one MTXPG in a cellular extract obtained from a human undergoing methotrexate therapy; and detecting at least one resolved MTXPG, thereby determining a level of the resolved MTXPG. A method of the invention can be useful, for example, for determining a level of $MTXPG_3$, $MTXPG_4$ or $MTXPG_5$, or for determining a level of each methotrexate polyglutamate species $MTXPG_1$ to $MTXPG_7$ present in the cellular extract. In one embodiment, the detection step does not include electrochemical detection. In another embodiment, the detection step does not include electrochemical detection or UV-visible spectrophotometry.

A variety of cellular extracts from a human undergoing methotrexate therapy can be useful in a method of the invention including, without limitation, red blood cell extracts and leukocyte extracts. In particular embodiments, a cellular extract useful in the invention is derived from a human having an autoimmune disease such as arthritis, systemic lupus erythematosus, or psoriasis, or from a human having cancer.

The methods of the invention can be useful for detection of low intracellular levels of methotrexate polyglutamates. In one embodiment, a method of the invention has a sensitivity of less than 500 nmol of each individual MTXPG species per liter packed red blood cells. In another embodiment, a method of the invention has a sensitivity of less than 50 nmol of each individual MTXPG species per liter packed red blood cells.

Further provided herein is a method for determining a level of a methotrexate polyglutamate in a cellular extract by resolving at least one MTXPG in the cellular extract, where the MTXPG contains no more than a natural abundance of radioactive isotopes; and detecting at least one resolved MTXPG, thereby determining a level of the resolved MTXPG, where detection of the resolved MTXPG does not require fractionation of the resolved MTXPG from other MTXPG species. In one embodiment, a method of the invention is used to determine a level of $MTXPG_3$, $MTXPG_4$ or $MTXPG_5$. In another embodiment, a method of the invention is used to determine a level of each $MTXPG_1$ to $MTXPG_7$ species, where detection of $MTXPG_1$ to $MTXPG_7$ does not require fractionation of the $MTXPG_1$ to $MTXPG_7$ species from each other.

The invention also provides a method for determining a level of a methotrexate polyglutamate in a cellular extract by resolving at least one MTXPG in the cellular extract, wherein said MTXPG contains no more than a natural abundance of radioactive isotopes; and detecting at least one resolved MTXPG, thereby determining a level of said resolved MTXPG, wherein said method detects less than 500 nmol of each individual MTXPG species per liter packed red blood cells. In one embodiment, the detection step does not include electrochemical detection. In another embodiment, the detection step does not include electrochemical detection or UV-visible spectrophotometry. A method of the invention can be useful for detecting, for example, less than 250 nmol, 100 nmol, 50 nmol, 20 nmol or 5 mol of each individual MTXPG species per liter packed red blood cells.

Cellular extracts useful in a method of the invention include, yet are not limited to, red blood cell extracts and leukocyte extracts. Cellular extracts useful in the invention further include, those from humans undergoing methotrexate therapy, and from humans having any of a variety of autoimmune diseases or cancers. In one embodiment, a method of the invention has a sensitivity of less than 500 nmol of each individual MTXPG species per liter packed red blood cells. In another embodiment, a method of the invention has a sensitivity of less than 50 nmol of each individual MTXPG species per liter packed red blood cells.

A variety of techniques for resolving at least one MTXPG and for detecting a resolved MTXPG can be useful in the above methods of the invention. A MTXPG can be resolved, for example, using chromatography such as high performance liquid chromatography (HPLC). A resolved MTXPG can be detected, for example, using fluorimetry, spectrophotometry or mass spectrometry, or a combination of these techniques.

The methods of the invention for determining a level of a methotrexate polyglutamate in a cellular extract are useful for analyzing intracellular levels of methotrexate metabolites in individuals undergoing methotrexate therapy. As used herein, the term methotrexate is synonymous with MTX and means a molecule having the structure shown in FIG. 1A. Methotrexate includes, in part, a 2,4-diamino substituted pterine ring moiety linked at the 6 position to the amino group of a p-aminobenzoyl moiety, the p-aminobenzoyl moiety having a methylated amino group and being amide bonded to a glutamic acid moiety. Consistent with the methotrexate polyglutamate nomenclature described below, "$MTXPG_1$" is synonymous with methotrexate.

Methotrexate is well known in the art as an inhibitor of dihydrofolate reductase (DHFR), which acts to decrease production of tetrahydrofolate (THF) from dihydrofolate (DHF). As a consequence, methotrexate indirectly inhibits purine and thymidine synthesis and amino acid interconversion. Methotrexate also exhibits anti-proliferative activity through inhibition of thymidylate synthesis, which is required to synthesize DNA (Calvert, *Semin. Oncol.* 26:3–10 (1999)). Methotrexate and its synthesis and properties are described in further detail in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; and 4,767,859. Methods of using methotrexate to treat cancer are described, for example, in U.S. Pat. Nos. 4,106,488, 4,558,690, and 4,662,359.

Methotrexate, which is useful in the treatment of a variety of autoimmune diseases and cancers, can be administered by oral or parenteral routes. The drug is readily distributed to body tissues, where it is transported into cells by a specific carrier system that includes components such as the reduced folate carrier, RCF1, and the folate receptor. Due to its high polarity at physiological pH, methotrexate does not readily pass through the cell membrane, and the majority of the drug enters cells via specific carriers. Once inside the cell, methotrexate is converted to methotrexate polyglutamates by specific enzymes such as folylpoly-gamma-glutamate synthetase, which add one or more glutamic acid moieties, linked by iso-peptidic bonds to the γ-carboxyl of methotrexate as described, for example, in Kamen, *Semin. Oncol.* S18:30–39 (1997).

The methods of the invention serve to determine a level of a methotrexate polyglutamate. As used herein, the term "methotrexate polyglutamate" is synonymous with "MTXPG" and means a derivative of methotrexate having two or more glutamates which are amide bonded to the p-aminobenzoyl moiety of methotrexate as shown in the generalized structure of FIG. 1B. The number of glutamates in a methotrexate polyglutamate varies from two to seven or more; the number of glutamate moieties can be denoted by "n" using the nomenclature $MTXPG_n$ such that, for example, $MTXPG_2$ is MTXPG having two glutamates, $MTXPG_3$ is MTXPG having three glutamates, $MTXPG_4$ is MTXPG having four glutamates, $MTXPG_5$ is MTXPG having five glutamates, $MTXPG_6$ is MTXPG having six glutamates, $MTXPG_7$ is MTXPG having seven glutamates, and $MTXPG_{2-7}$ is a mixture containing $MTXPG_2$, $MTXPG_3$, $MTXPG_4$, $MTXPG_5$, $MTXPG_6$ and $MTXPG_7$ with the ratio of the individual polyglutamated forms in the mixture not defined.

The methods of the invention are useful for determining a level of a methotrexate polyglutamate in a cellular extract. The term "level," as used herein, means the amount or concentration of the methotrexate polyglutamate in the cellular extract. It is understood that a level can be an absolute level such as a molar concentration or weight or a relative level such as a percent or fraction compared to one or more other molecules in the cellular extract. Specifically excluded from the definition of "level," as used herein, are estimates or measurements based on enzymatic activity, such as inhibition of dihydrofolate reductase or other another folate-dependent enzyme.

As used herein in reference to a methotrexate polyglutamate, the term "resolved" means sufficiently separated from other molecules to allow determination of a level of the methotrexate polyglutamate. Thus, a methotrexate polyglutamate species having an observable property is resolved by sufficiently separating the MTXPG species from other molecules having the same property. As a non-limiting example, a MTXPG species detectable by fluorescence at a particular excitation and emission wavelength can be resolved by separating it from other molecules that have substantial excitation and emission at the same wavelengths; the MTXPG species may or may not be separated from a variety of other molecules having different excitation and emission wavelengths. In view of the foregoing, it is understood that whether or not a methotrexate polyglutamate is resolved is determined, in part, by the detection means utilized in the method.

As disclosed herein, methotrexate polyglutamates were chromatographically resolved from other cellular components using reverse phase chromatography as set forth in Examples I and II and subsequently quantitated, for example, by comparison to one or more known reference standards. As demonstrated herein, chromatographic resolution of methotrexate polyglutamates can be performed by passing a mixture of methotrexate polyglutamates in a cellular extract through a C18 reverse phase column in a mobile phase consisting of a 20 minute linear gradient from 2% acetonitrile/98% mobile phase A to 12.5% acetonitrile/87.5% mobile phase A, wherein mobile phase A is 10 mM ammonium acetate, pH 6.5, with hydrogen peroxide at a final concentration of 0.2% (Examples I and II).

A reverse phase column useful for resolving a mixture of MTXPGs in a cellular extract can have, for example, dimensions of 25 cm×4.6 mm, as exemplified herein. It is understood that columns having larger or smaller diameters, lengths or both can also be used, for example, to accommodate larger or smaller sample sizes. Flow rates can vary, without limitation, from 0.2 to 2.5 ml/minute. As demonstrated herein, the flow rate for the mobile phase was 1 ml/minute. However, the flow rate of the mobile phase can be altered as desired. A slower flow rate, such as 0.8 ml/minute, 0.5 ml/minute or 0.2 ml/minute, can be used, for example, with a smaller column or to increase methotrexate polyglutamate retention times. Alternatively a faster flow rate, such as 1.5 ml/minute or 2.0 ml/minute, can be used, for example, with a larger column or to decrease methotrexate polyglutamate retention times.

A methotrexate polyglutamate can be resolved from the components of a cellular extract by any of a variety of methods including chromatographic and spectrometric methods and other methods such as those that serve to separate molecules based on size or charge. Examples of useful chromatographic methods include, but are not limited to, liquid and gas phase chromatographic methods such as, without limitation, ion exchange chromatography, size exclusion chromatography, iso-electric focusing, gel electrophoresis, capillary electrophoresis, normal phase chromatography, reverse phase chromatography and affinity chromatography. Exemplary, but not limiting, spectrometric methods are mass spectrometry, tandem mass spectrometry, and preparative mass spectrometry with electrospray ionization. It is understood that, if desired, two or more different techniques can be combined to resolve at least one MTXPG in a method of the invention. As a non-limiting example, soluble molecules can be separated from proteins and other precipitated materials after cell lysis and perchloric acid precipitation, followed by high performance liquid chromatography of the soluble molecules.

A cellular extract derived from cells or an individual treated with methotrexate typically contains a mixture of methotrexate polyglutamated species, which differ in the number of attached glutamate moieties. As used herein, the term "cellular extract" means a mixture containing a heterogenous plurality of cellular components. A cellular extract useful in the invention can contain, for example, a heterogeneous plurality of soluble cellular compounds, proteins and metabolites and can be derived from a single cell type, mixture of cell types or tissue source. Heterogeneity of a cellular extract can be characterized by various criteria. According to one criteria, a cellular extract useful in the invention is heterogeneous with respect to the variety of cellular components present in the extract; such a cellular extract can contain, without limitation, at least 100, 1000, $1 \times 10^4$ or $1 \times 10^5$ or more different cellular components, for example, at least 100, 1000, $1 \times 10^4$ or $1 \times 10^5$ or more different cellular proteins. Heterogeneity can also be expressed a percentage of the total number of different components of the cell from which the extract is derived. As an example, a cellular extract can contain cellular components representing at least 5%, 10%, 15%, 20%, 25%, 50% or 75% of the variety of components present in the cell from which the extract was derived. Heterogeneity can also be determined based on the percentage of any one cellular component in a cellular extract compared to the totality of other components in the cellular extract. Thus, a cellular extract useful in the invention can be a mixture in which any one cellular component represents at most 90%, 80%, 70%, 60%, 50%, 25%, or 10% of totality of other cellular components by weight in the extract. A cellular extract useful in a method of the invention can contain mixtures of components such as proteins, components that are larger than 100 Da or components that absorb radiation between about 303 nm and 313 nm or at about 370 nm.

A cellular extract useful in a method of the invention can be any cellular extract that contains one or more methotrexate polyglutamates. It is understood that additional exogenous methotrexate polyglutamates can be added, if desired, to a cellular extract. The addition of one or more exogenous MTXPGs into a cellular extract can be useful for determining a standard curve for quantification or for optimizing detection conditions. A cellular extract containing methotrexate polyglutamates can be obtained by adding methotrexate to cells and allowing polyglutamation to occur in vitro. Thus, a method of the invention can be used to monitor or determine polyglutamation activity of a cell or a component thereof, such as folylpoly-gamma-glutamate synthetase. Cellular extracts also can be prepared from a cell isolated from an individual that has been administered methotrexate by any route.

Cellular extracts useful in the invention can be prepared from a cell or tissue using methods well known in the art. Those skilled in the art will know or be able to determine an appropriate method for obtaining source cells based on their location and characteristics. As an example, red blood cells and other blood cells can be obtained by harvesting through intravenous routes. Cells can also be removed from tissues, such as cancer tissues, using known biopsy methods including, for example, those utilizing an open surgical incision, biopsy needle or endoscope. Cells can be lysed by any of a variety of means depending, in part, on the properties of the cell. As non-limiting examples, cells can be lysed by mechanical disruption with glass beads, a Dounce homogenizer, french press, or sonication; enzymatic disruption with lysozyme or other enzyme that degrades the cell wall; osmotic disruption or a combination of these methods.

A cellular extract useful in a method of the invention can be a partially purified extract, which can be, for example, enriched in methotrexate polyglutamates. As an example, an extract can be partially purified by centrifugation to remove insoluble material such as membranes and large cellular structures (see Example I). Partial purification to separate cellular components including methotrexate polyglutamates or analogs thereof from other cellular components can include, without limitation, centrifugation, protein precipitation, liquid-liquid extraction, solid-phase extraction, or chromatography such as reverse phase chromatography, ion pairing chromatography or ion exchange chromatography, as described, for example, in Rubino, *J. Chromatog.* 764:217–254 (2001). Additional methods that can be used to obtain and partially purify cellular extracts are well known in the art, as described, for example, in Scopes, *Protein Purification: Principles and Practice*, 3$^{rd}$ Ed., Springer-Verlag, New York (1994) and Coligan et al., *Current Protocols in Protein Science*, John Wiley and Sons, Baltimore, Md. (2000).

In a method of the invention, proteinaceous material can be precipitated away from methotrexate polyglutamates and other metabolites, and the protein-depleted supernatant subjected to further separation procedures. As used herein, the term "acid" refers to a reagent that is capable of effecting preferential precipitation of proteinaceous material from solution, without precipitating methotrexate polyglutamates. One skilled in the art understands that an acid useful in the invention does not substantially destroy, degrade or otherwise affect detection of the methotrexate polyglutamates. Exemplary acids useful in the invention include, without limitation, perchloric acid; sulfuric acid, phosphoric acid and glacial acetic acid. Additional acids useful in the invention can be identified by the ability to yield substantially similar methotrexate polyglutamate level for a particular sample, as compared to a sample contacted with 70% perchloric acid.

The methods of the invention are well suited to determining a level of a methotrexate polyglutamate in a red blood cellular extract as demonstrated in Examples I and II. The conditions exemplified herein can also be readily applied to other types of cellular extracts in order to determine a level of a methotrexate polyglutamate. It is understood that the cellular extract can be from a cell that is a target for methotrexate therapy or otherwise is a cell indicative of efficacy or toxicity of methotrexate therapy. Non-limiting examples of cellular extracts that are useful in the invention include extracts prepared from tissue biopsies, erythrocytes, neutrophils and leukocytes. Additional cellular extracts useful in the invention include, without limitation, neoplastic or cancer cell extracts such as those obtained from any of the specific cancers set forth below. Cellular extracts useful in a method of the invention further include, but are not limited to, eukaryotic cellular extracts, mammalian cellular extracts, primate cellular extracts, human cellular extracts, non-human primate cellular extracts, rat cellular extracts, mouse cellular extracts, cat cellular extracts, dog cellular extracts, bird cellular extracts and horse cellular extracts.

A cellular extract useful in the invention can be obtained, for example, from the cells of any individual treated with methotrexate therapy, including low-dose or high-dose therapy. In one embodiment, a cellular extract useful in a method of the invention is from a human having an autoimmune disease. As used herein, the term "autoimmune disease" means a disease resulting from an immune response against a self tissue or tissue component and includes a self antibody response or cell-mediated response. The term autoimmune disease, as used herein, encompasses organ-specific autoimmune diseases, in which an autoimmune response is directed against a single tissue, such as Crohn's disease and ulcerative colitis, Type I diabetes mellitus, myasthenia gravis, vitiligo, Graves' disease, Hashimoto's disease, Addison's disease and autoimmune gastritis; and autoimmune hepatitis. The term autoimmune disease also encompasses non-organ specific autoimmune diseases, in which an autoimmune response is directed against a component present in several or many organs throughout the body. Such autoimmune diseases include, for example, rheumatoid disease, systemic lupus erythematosus, progressive systemic sclerosis and variants, polymyositis and dermatomyositis. Additional autoimmune diseases include, but are not limited to, pernicious anemia, autoimmune gastritis, primary biliary cirrhosis, autoimmune thrombocytopenia, Sjögren's syndrome, multiple sclerosis and psoriasis. One skilled in the art appreciates that the autoimmune diseases set forth above have been treated with methotrexate therapy or can be treated with methotrexate therapy and further recognizes that the methods of the invention can be used with a cellular extract obtained from a human or other mammal having any of the above or another autoimmune disease.

In one embodiment, a cellular extract useful in a method of the invention is obtained from a human having arthritis. As used herein, the term "arthritis" means an inflammatory condition that affects joints. Arthritis can be, without limitation, infective, autoimmune or traumatic in origin; the term arthritis includes, but is not limited to, acute arthritis, acute gouty arthritis, bacterial arthritis, chronic inflammatory arthritis, degenerative arthritis (osteoarthritis), infectious arthritis, juvenile arthritis, mycotic arthritis, neuropathic arthritis, polyarthritis, proliferative arthritis, psoriatic arthritis, juvenile rheumatoid arthritis, venereal arthritis, and viral arthritis.

In a further embodiment, a cellular extract useful in a method of the invention is obtained from a human having rheumatoid arthritis. Rheumatoid arthritis is a chronic systemic disease primarily of the joints, usually polyarticular, marked by inflammatory changes in the synovial membranes and articular structures and by muscle atrophy and rarefaction of the bones. Methotrexate is widely used in the treatment of rheumatoid arthritis, and one skilled in the art recognizes that the methods of the invention can be practiced with a cellular extract from a human or other mammal having rheumatoid arthritis or another form of arthritis.

In another embodiment, a method of the invention is practiced with a cellular extract from a human having cancer. As used herein, the term "cancer" is intended to mean any member of a class of diseases characterized by the uncontrolled growth of aberrant cells. The term includes all known cancers and neoplastic conditions, whether characterized as malignant, benign, soft tissue or solid, and cancers of all stages and grades including pre- and post-metastatic cancers. The term cancer encompasses, without limitation, leukemias such as acute lymphocytic leukemia and acute myelocytic leukemia; lymphomas; choriocarcinomas; head and neck cancers; and osteogenic sarcomas, each of which are widely treated with methotrexate. The term cancer further includes, but is not limited to, digestive and gastrointestinal cancers such as anal cancer, bile duct cancer, gastrointestinal carcinoid tumors and colon cancer; esophageal cancer, gallbladder cancer, liver cancer, pancreatic cancer, rectal cancer, appendix cancer, small intestine cancer and stomach (gastric) cancer; breast cancer; ovarian cancer; lung cancer; renal cancer; cancer of the central nervous system; and skin cancer. In one embodiment, a method of the invention is practiced with a cellular extract obtained from a human having leukemia.

Rheumatoid arthritis and a variety of other autoimmune disorders such as psoriasis, systemic lupus erythematosus, and graft-versus-host disease are typically treated with low-dose methotrexate therapy, which is also used in some cancer treatment regimens. In one embodiment, a method of the invention is practiced with a cellular extract from a human undergoing low-dose methotrexate therapy. As used herein, the term "low-dose MTX therapy" means administration of methotrexate to a human at a dose that is less than 40 mg/m$^2$ of body surface per week. Typically, low-dose methotrexate therapy is administered orally at a dose in the range of 2.5 to 40 mg/m$^2$ of body surface per week, for example, 2.5 to 25 mg/m$^2$ of body surface per week depending upon the condition being treated.

The methods of the invention can also be useful for determining a level of a methotrexate polyglutamate in a cellular extract from a human undergoing high-dose methotrexate therapy. As used herein, the term "high-dose MTX therapy" means administration of methotrexate to an individual at a dose that is at least 40 mg/m$^2$ of body surface per day, for example, at least 100, 500, 1000, 1500, 3000 mg/m$^2$ or 5000 mg/m$^2$ of body surface per day. One skilled in the art understands that high-dose methotrexate therapy is frequently used as an anti-cancer therapeutic and can be administered at doses up to 5 g/m$^2$ of body surface per day or higher depending upon the condition or disease being treated. One skilled in the art recognizes that the doses of methotrexate typically used in high-dose MTX therapy can be administered, for example, intravenously or orally and that such high-dose methotrexate therapy generally requires a period of recovery, which can include leucovorin rescue or another form of folate replacement.

It will be understood that the dosage ranges of methotrexate set forth above in the definitions of high-and low-dose methotrexate therapy are generalized with respect to treatment of a variety of diseases and that the range of methotrexate dose that is administered for one disease can differ from the range administered for another. Accordingly, a dose of 40 mg/m$^2$ of body surface per day, although generally considered high-dose MTX therapy, may be considered by those skilled in the art of cancer therapy as a relatively low dose for treating cancer. Similarly, a dose of 30 mg/m$^2$ of body surface per day, although generally considered as low-dose MTX therapy, may be considered by those skilled in the art of rheumatology as a relatively high-dose for treating rheumatoid arthritis.

The methods of the invention also can be used to detect metabolites of a methotrexate analog or other polyglutamylatable antifolate. As used herein, the term "antifolate" means a molecule having structural similarity to folate and activity as a folate antagonist against one or more folate-dependent enzymes. Polyglutamylatable antifolates are antifolates that can be polyglutamated in a cell by an enzyme such as folylpoly-gamma-glutamate synthetase. Examples of polyglutamylatable antifolates include, without limitation, aminopterin, raltitrexed, lometrexol, multitargeted antifolate (MTA), AQA, MTX and analogs thereof. Aminopterin, for example, possesses a hydrogen instead of a methyl group at position N-10 compared to the structure of methotrexate. Raltitrexed is a selective inhibitor of thymidylate synthase as described, for example, in Kamen, *Semin. Oncol.* S18:30–39 (1997). Lometrexol selectively inhibits glycinamide ribonucleotide formyltransferase, the first enzyme involved in the pathway of de novo purine synthesis as described, for example, in Calvert, supra, 1999. Multi-targeted antifolate is an inhibitor of multiple folate-dependent enzymes, such as dihydrofolate reductase, thymidylate synthase, and glycinamide ribonucleotide formyltransferase (see, for example, Calvert, supra, 1999).

In one embodiment, the methods of the invention are useful for detecting polyglutaminated forms of a methotrexate analog. As used herein, the term "methotrexate analog" means a molecule having structural and functional similarity to methotrexate. Methotrexate analogs are functionally characterized, in part, by their inhibitory activity against dihydrofolate reductase. A methotrexate analog useful in the invention acts as a substrate for polyglutamation in a cell by an enzyme such as folylpoly-gamma-glutamate synthetase. Methotrexate analogs include, but are not limited to, 4-amino derivatives with halogen substitution on the para-aminobenzoic moiety, such as dichloromethotrexate (see, for example, Frei et al., *Clin. Pharmacol. Therap.* 6:160–71 (1965)); 7-methyl substituted MTX (see, for example, Rosowsky and Chen, *J. Med. Chem.* 17:1308–11 (1974)); 3',5'-difluoro MTX, (see, for example, Tomcuf, *J. Organic Chem* 26:3351 (1961)); 2' and 3' monofluorinated derivatives of aminopterin (see, for example, Henkin and Washtien, *J. Med. Chem.* 26:1193–1196 (1983)); and 7,8-dihydro-8-methyl-MTX (see, for example, Chaykovsky, *J. Org. Chem.* 40:145–146 (1975)). The skilled person understands that the methods of the invention can be used to optimize or monitor efficacy or toxicity associated with methotrexate analog therapy or other polyglutamylatable antifolate therapy in the same manner as disclosed herein for monitoring methotrexate therapy.

The present invention also provides a method for determining a level of a methotrexate polyglutamate in a cellular extract by resolving at least one MTXPG in the cellular extract; irradiating the at least one MTXPG, thereby producing at least one resolved fluorescent MTXPG photolytic product; and detecting the at least one resolved fluorescent MTXPG photolytic product, thereby determining a level of the MTXPG. A method of the invention can be useful, for example, for determining a level of MTXPG$_3$, MTXPG$_4$ or MTXPG$_5$, or for determining a level of each MTXPG$_1$ to MTXPG$_7$ species present in the cellular extract.

An MTXPG can be resolved, for example, using chromatography such as high performance liquid chromatography. In a method of the invention, the MTXPG can be irradiated, for example, using UV irradiation. In one embodiment, the MTXPG is UV irradiated in a solvent having 0.05% to 1% H$_2$O$_2$. In another embodiment, the MTXPG is UV irradiated in a solvent having 0.1% to 0.3% H$_2$O$_2$. In a further embodiment, the MTXPG is UV irradiated using radiation having a wavelength in the range of 225 nm to 275 nm, for example, a wavelength of 254 nm. The irradiation can have a duration, for example, of 0.5 to 60 seconds or 0.5 to 15 seconds.

In a method of the invention, detecting a resolved fluorescent MTXPG photolytic product can involve, for example, detecting fluorescence upon excitation in the range of 240 nm to 420 nm. In particular embodiments, fluorescence is detected upon excitation with UV radiation in the range of 240 nm to 300 nm, for example, upon excitation with UV radiation at 274 nm. In another embodiment, fluorescence is detected upon excitation with UV radiation in the range of 360 nm to 410 nm. It is understood that fluorescence is detected at an appropriate emission wavelength, such as an emission wavelength in the range of 320 nm to 550 nm or an emission wavelength in the range of 440 nm to 500 nm. In one embodiment, fluorescence is detected at an emission wavelength of 464 nm. In a further embodiment, fluorescence is detected upon excitation with UV radiation at 274 nm and at an emission wavelength of 464 nm.

A variety of cellular extracts can be useful in a method of the invention including, without limitation, human cellular extracts, red blood cell extracts and leukocyte extracts. Such cellular extracts can be derived from a human undergoing methotrexate therapy, including, but not limited to, a human undergoing low-dose methotrexate therapy. In particular embodiments, the cellular extract is derived from a human having an autoimmune disease such as arthritis, rheumatoid arthritis, polyarthritis, systemic lupus erythematosus or psoriasis, or from a human having cancer. A method of the invention can have a sensitivity, for example, of less than 500 nmol of each individual MTXPG species per liter packed red blood cells, or less than 50 nmol of each individual MTXPG species per liter packed red blood cells.

As disclosed herein, fluorescent MTXPG photolytic products can be produced by irradiation of methotrexate polyglutamates. The term "photolytic product," as used herein, means a molecule that is produced by cleavage of bonds in a methotrexate polyglutamate that is electronically excited by radiation. The process of producing a photolytic product is referred to as photolysis. Photolysis of one or more MTXPGs to produce one or more "MTXPG photolytic products" can be performed, for example, with UV light, which is a term understood in the art to include light of any wavelength in the range of about 200 to 400 nm. It further is understood that any light source which produces UV light can be useful for irradiating methotrexate polyglutamates in a method of the invention including, for example, a lamp such as an arc lamp or quartz halogen lamp, or a laser. As demonstrated in Example II, fluorescent MTXPG photolytic products were produced by irradiating MTXPGs with a low pressure mercury UV lamp which emits radiation in the range of 225 to 275 nm, with a peak output at 254 nm. It is understood that MTXPGs can be selectively irradiated with a particular wavelength in the UV range by using an appropriate light source, optical filter or combination of these components in accordance with their known optical characteristics.

In a method of the invention which involves detecting a resolved fluorescent MTXPG photolytic product, at least one MTXPG is irradiated for an appropriate period of time to yield a fluorescent MTXPG photolytic product. In particular embodiments, a method of the invention is practiced by irradiating at least one MTXPG for 0.5 to 60 seconds, or for 0.5 to 15 seconds. As non-limiting examples, a method of the invention can be practiced by irradiating at least one MTXPG for 0.1 to 100 seconds, 0.2 to 60 seconds, 0.5 to 60 seconds, 0.5 to 45 seconds, 0.5 to 30 seconds, 0.5 to 20 seconds, 0.5 to 15 seconds, 0.5 to 10 seconds, 1 to 20 seconds, 1 to 10 seconds, 2 to 20 seconds or 2 to 10 seconds. As additional non-limiting examples, a method of the invention can be practiced by irradiating at least one MTXPG for 0.5 to 6 seconds, 0.5 to 5 seconds, 0.5 to 4 seconds, 1 to 6 seconds, 1 to 5 seconds, 1 to 4 seconds, or 2 to 4 seconds. In particular embodiments, a method of the invention is practiced by irradiating at least one MTXPG for 0.5 to 60 seconds, 0.5 to 15 seconds, or 2 to 4 seconds.

As disclosed herein, irradiation of methotrexate polyglutamates for three seconds with a 254 nm low pressure mercury ultraviolet lamp produced fluorescent MTXPG photolytic products with overlapping excitation spectra, readily detectable, for example, upon excitation with UV radiation with a wavelength of 274 nm and at an emission wavelength of 464 nm. See, for example, Example I and FIG. 2B. It is understood that the time of irradiation can be varied to produce the desired fluorescent MTXPG photolytic product having characteristic properties as desired for a particular application. A particular fluorescent photolytic product can have, for example, one or more characteristic properties such as characteristic fluorescence excitation and emission peak maxima, and characteristic fluorescence intensity levels depending, for example, upon the pH and amount of acetonitrile present during detection.

Photolysis of methotrexate polyglutamates can be carried out in the presence of hydrogen peroxide ($H_2O_2$) or another peroxide. As a non-limiting example, when hydrogen peroxide during irradiation of $MTXPG_5$ is added, the final concentration can be about 0.03% or higher. In particular embodiments, the final concentration of hydrogen peroxide during photolysis of MTXPGs is in the range of 0.05% to 1%, 0.1% to 1%, 0.1% to 0.5% or 0.1% to 0.3%.

A level of a particular methotrexate polyglutamate in a cellular extract can be determined based on the level of the corresponding resolved fluorescent MTXPG photolytic product. As one example, the amount or concentration of the fluorescent MTX photolytic product can be determined based on the intensity of fluorescence from the photolytic product as illustrated in the examples below. As used herein, the term "fluorescence" means an emission of photons in the ultraviolet (UV), visible (VIS) or infrared (IR) region of the spectrum in response to electronic excitation by radiation. The term "fluorescent," when used in reference to a MTXPG photolytic product, means a photolytic product that emits photons in the UV, VIS or IR region of the spectrum in response to electronic excitation by radiation. Thus, a fluorescent MTXPG photolytic product is a photolytic product derived from a methotrexate polyglutamate that emits photons in the UV, VIS or IR region of the spectrum in response to electronic excitation by radiation. A fluorescent MTXPG photolytic product can be characterized, for example, as emitting photons at a quantum yield of at least 0.01 when excited by radiation in solution. In particular embodiments, a fluorescent MTXPG photolytic product is characterized by a quantum yield of fluorescence that is at least 0.1, 0.2, 0.3, 0.4, 0.5, 0.6, 0.7, 0.8, 0.9 or higher when excited by radiation in solution.

A fluorescent molecule, such as a fluorescent MTXPG photolytic product, also can be characterized with respect to its maximum emission wavelength or maximum excitation wavelength. In particular embodiments, a method of the invention involves detecting a resolved fluorescent MTXPG photolytic product having a maximum excitation wavelength in the infrared, red, orange, yellow, green, blue, violet or ultraviolet region of the spectrum. In additional embodiments, a method of the invention is practiced by detecting a resolved fluorescent MTXPG photolytic product having a maximum emission wavelength in the infrared, red, orange, yellow, green, blue, violet or ultraviolet region of the spectrum.

Figure 2:
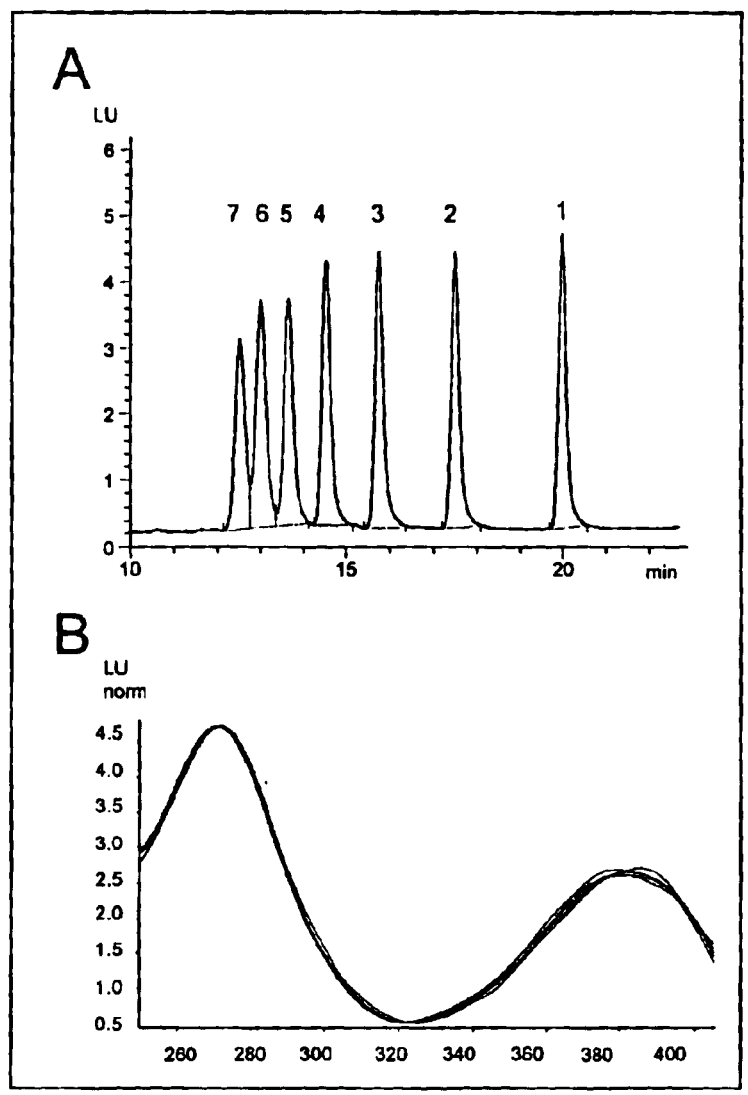
FIG. 2 shows a chromatogram of methotrexate and methotrexate polyglutamates in water and excitation spectra of the photolytic products of these analytes. (A) Chromatogram of a standard in water containing all seven methotrexate polyglutamates at a final concentration of 25 nmol/L each. (B) Excitation spectra of photolytic products of $MTXPG_1$ through $MTXPG_7$ in water.

Fluorescence can be detected in a method of the invention using any of a variety of excitation sources and emission detectors. Excitation of a fluorescent MTXPG photolytic product can be achieved, for example, with an excitation source such as a lamp or laser including, without limitation, any of those described above in regard to photolysis. Excitation at a particular wavelength or in a particular wavelength range can be achieved in a method of the invention using, for example, a laser that is tuned to the desired wavelength or a lamp having an output that includes the desired wavelength range. An appropriate optical filter can be placed between the excitation source and fluorescent MTXPG photolytic product to further limit the range of wavelengths contacting the fluorescent MTXPG photolytic product if desired. As shown in FIG. 2B and set forth in Example I, each of the seven fluorescent $MTXPG_1$ to $MTXPG_7$ photolytic products has two excitation peaks in the range of 240 nm to 420 nm, including a peak from about 240 nm to 300 nm and a peak from about 360 nm to 410 nm. In particular embodiments of the invention, a fluorescent MTXPG photolytic product can be detected by excitation at a wavelength in the range of about 240 nm to 420 nm, about 240 nm to 300 nm or about 360 nm to 410 nm. If desired, the methods of the invention can include excitation at or near the peak of 274 nm or in a range near this peak including, for example, excitation at a wavelength in the range of 250 nm to 300 nm or 260 nm to 285 nm. Excitation at or near the peak of 385 nm or in a range near this peak can also be useful in a method of the invention including, for example, excitation at a wavelength in the range of 360 nm to 400 nm or 375 nm to 395 nm.

Emission can be detected from a fluorescent MTXPG photolytic product using any of a variety of detectors such as, without limitation, a photomultiplier tube, diode, diode array or charge coupled device camera. A detector that detects light at a particular wavelength or in a particular wavelength range can be useful in a method of the invention. If desired, an optical filter can be placed between the fluorescent MTXPG photolytic product and the detector to limit the range of wavelengths detected. As disclosed herein, fluorescent $MTXPG_1$ to $MTXPG_7$ photolytic products emit from about 320 nm to 550 nm and have a primary emission peak from about 440 nm to 520 nm. In particular embodiments of the invention, emission from a fluorescent MTXPG photolytic product can be detected at a wavelength in the range of about 320 nm to 550 nm or about 440 nm to 520 nm. If desired, the methods of the invention can include detection of emission at or near the peak of 464 nm or in a range near this peak including, for example, emission at a wavelength in the range of 430 nm to 510 nm or 450 nm to 480 nm.

The content of a solution that is used to detect a resolved MTXPG, or a photolytic product thereof, can be varied, for example, with respect to pH or acetonitrile content. The pH at which a MTXPG, or a photolytic product thereof, is detected in a method of the invention can be in the range of, for example, about pH 2 to 8 or in the range of about pH 4 to 7. In particular embodiments, a MTXPG, or a photolytic product thereof, can be detected, for example, at pH 4, 4.5, 5, 5.5, 6, 6.5 or 7. The amount of acetonitrile present during detection of the MTXPG, or a photolytic product thereof, can be in the range of, for example, about 0% to 20% or about 10% to 20%. In particular embodiments, the amount of acetonitrile present can be, for example, 5%, 10%, 15% or 20%, or 11%, 11.5%, 12%, 12.5%, 13% or 13.5%.

A resolved methotrexate polyglutamate can also be detected in a method of the invention based on one or more other observable, characteristic properties of the methotrexate polyglutamate including, for example, ultraviolet or visible light absorption properties, fluorescence, electrochemical properties, or mass. As non-limiting examples, a resolved MTXPG can be detected with UV/Vis absorption spectroscopy, fluorimetry, electrochemical detection, or mass spectrometry. Those skilled in the art will know or be able to determine an appropriate means for detecting methotrexate polyglutamates based on the accuracy and sensitivity desired and the presence of potentially interfering substances in the particular cellular extract being analyzed.

Sufficient intracellular levels of methotrexate polyglutamates can be associated with efficacy, and higher levels can be associated with toxicity. By determining the intracellular level of one or more methotrexate polyglutamates, the methods of the invention can be useful for adjusting the amount or frequency of methotrexate therapy in order that the methotrexate polyglutamates remain within the therapeutic range, such that undesirable toxic side effects can be avoided while efficacy is achieved.

Thus, the present invention provides a method of optimizing therapeutic efficacy or reducing toxicity associated with methotrexate therapy administered to a human by resolving at least one MTXPG in a cellular extract obtained from the human; detecting at least one resolved MTXPG, thereby determining a level of the resolved MTXPG; and selecting a drug or dosage to be subsequently administered to the human based on the level of the resolved MTXPG. A method of the invention can be useful, for example, for determining a level of $MTXPG_3$, $MTXPG_4$ or $MTXPG_5$, or for determining a level of each $MTXPG_1$ to $MTXPG_7$ species present in the cellular extract. A method of the invention can involve altering a methotrexate dosage subsequently administered to the human, for example, reducing or increasing a methotrexate dosage subsequently administered to the human, or altering a dose of folic acid, or a derivative thereof, subsequently administered to the human.

Cellular extracts useful in a method of the invention include, yet are not limited to, red blood cell extracts; leukocyte extracts; cellular extracts from humans undergoing methotrexate therapy; and cellular extracts from humans having any of a variety of autoimmune diseases or cancers. Cellular extracts useful in the invention include, without limitation, those derived from a human having an autoimmune disease such as arthritis, rheumatoid arthritis, polyarthritis, systemic lupus erythematosus or psoriasis, or from a human having cancer. In one embodiment, a method of the invention has a sensitivity of less than 500 nmol of each individual MTXPG species per liter packed red blood cells. In another embodiment, a method of the invention has a sensitivity of less than 50 nmol of each individual MTXPG species per liter packed red blood cells.

In a method of the invention for optimizing therapeutic efficacy or reducing toxicity, a MTXPG can be resolved, for example, using chromatography such as high performance liquid chromatography. A resolved MTXPG can be detected using one or more techniques such as, without limitation, fluorimetry, spectrophotometry or mass spectrometry. It is understood that such detection techniques can be combined with chromatography or other means for resolving at least one MTXPG in a cellular extract.

Any of a variety of types of cellular extracts such as those described hereinabove can be useful in a method of the invention for optimizing therapeutic efficacy or reducing toxicity associated with methotrexate therapy. Cellular extracts can be prepared from any cell or tissue that is indicative of the efficacy or toxicity of methotrexate therapy such as a diseased cell or tissue, a target cell for methotrexate therapy or a cell that is representative of the amount of drug in diseased cells. As used herein, the term "target cell for methotrexate therapy" means a cell for which uptake of methotrexate is desired to treat a disease or condition. As non-limiting examples, cell extracts can be prepared from red blood cells, leukocytes, neutrophils, cancer cells, and tissue biopsies.

A method of the invention for optimizing therapeutic efficacy or reducing toxicity associated with methotrexate therapy can further include altering the methotrexate dosage subsequently administered to the human based on the determined level of methotrexate polyglutamates. Where the determined level of one or more methotrexate polyglutamates is below a therapeutic range, the dose or frequency of methotrexate administered to the human can be increased. Similarly, where the determined level of one or more methotrexate polyglutamates is above a therapeutic range, the dose or frequency of methotrexate administered to the human can be reduced to avoid toxicity. A therapeutic range can be determined from dose-response information for a particular disease or condition and, if desired, for the age, gender or medical condition of the human being treated. As an example, a level of a MTXPG determined in a red blood cellular extract can be compared to dose-response information correlating red blood cell methotrexate polyglutamate levels with reduction of an arthritis symptoms. Dose-response information also can be obtained using well known clinical procedures relevant to the particular pathological condition.

In a particular embodiment of the invention, a cellular extract useful in a method of the invention for optimizing therapeutic efficacy or reducing toxicity associated with methotrexate therapy can be obtained from a non-target cell for methotrexate therapy. As used herein, the term "non-target cell for methotrexate therapy" means a cell for which uptake of methotrexate is not desired. Such a non-target cell can be a normal cell that is sensitive to levels of MTX or that is disposed to take up methotrexate administered by a particular route. One skilled in the art understands that a MTXPG level in cellular extracts from non-target cells can be representative of the level in target cells and, thus, can be useful for optimizing therapeutic efficacy or reducing toxicity associated with methotrexate therapy.

Methotrexate therapy can cause a variety of adverse effects that mimic folate deficiency including, for example, gastrointestinal intolerance, stomatitis, alopecia and cytopenia. Many adverse effects of methotrexate therapy are dose dependent and can be alleviated by administration of compensatory doses of folic acid, folinic acid or a folic acid analog. Accordingly, a method of the invention for optimizing therapeutic efficacy or reducing toxicity associated with methotrexate therapy can further include, if desired, altering the dose of folate or a folic acid analog subsequently administered to the human based on the determined level of intracellular methotrexate polyglutamates. Folic acid analogs useful in the invention include, without limitation, folic acid, dihydrofolic acid, tetrahydrofolic acid, 5-formyl-tetrahydrofolic acid and 10-methyl-tetrahydrofolic acid.

The following examples are intended to illustrate but not limit the present invention.

EXAMPLE I

An HPLC System Suitable for Detection of Methotrexate Polyglutamates in Samples from Individuals Undergoing Low-Dose Methotrexate Therapy This example describes a chromatographic system, conditions and reagents suitable for separation of methotrexate polyglutamates in cell samples.

A. Preparation of Reagents 4-amino-10-methylpteroylglutamic acid (methotrexate; $MTXPG_1$) was purchased from SIGMA (St. Louis, Mo.). 4-amino-10-methylpteroyldi-glutamic acid ($MTXPG_2$), 4-amino-10-methylpteroyltri-glutamic acid ($MTXPG_3$), 4-amino-10-methylpteroyltetra-glutamic acid ($MTXPG_4$), 4-amino-10-methylpteroylpenta-glutamic acid ($MTXPG_5$), 4-amino-10-methylpteroylhexa-glutamic acid ($MTXPG_6$), and 4-amino-10-methylpteroylhepata-glutamic acid ($MTXPG_7$) were purchased as ammonium salts from Schircks laboratories (Jona, Switzerland). HPLC grade acetonitrile was purchased from Fisher Chemicals (Fair Lawn, N.J.); hydrogen peroxide (30%, v/v), ammonium hydroxide, and glacial acetic acid were obtained from Sigma.

Methotrexate and each of the individual purified methotrexate polyglutamates were dissolved in 0.1 N potassium hydroxide. After dissolution, the concentration of the standards was confirmed using a Hitachi U-2000 spectrophotometer and the UV molar extinction coefficients ($\epsilon 256$ nm=23,000). The individual purified methotrexate polyglutamate standards were diluted to a final concentration of 100 $\mu$M in water and stored at −70° C., where they were stable for at least 6 months.

B. Chromatographic System and Separation

The liquid chromatograph was an Agilent 1100 HPLC chemstation system composed of a quaternary pump, a system controller, an autoinjector, a sample cooler kept at 4° C., and a fluorometer. Chromatograms were acquired and analyzed on a Hewlett-Packard Vector XA computer. Methotrexate polyglutamates were detected with post-column derivatization using a photochemical reactor unit (Aura Industries; New York, N.Y.) equipped with an elongated 254 nm low pressure mercury ultraviolet lamp and containing a 1/16" outer diameter TEFLON™ tubing (internal diameter 0.25 mm) assembled as a knitted coil and connected on-line between the analytical column and fluorometer. The knitted coil was extended lengthwise through the photochemical reactor unit; all but a portion of the elongated lamp was masked with foil such that only a segment of the knitted coil was irradiated. In particular, the lamp was masked such that only 1 meter of the coil was irradiated with the lamp, which at a flow rate of 1 ml/min corresponded to 3 seconds irradiation. Methotrexate polyglutamate photolytic products were measured at an excitation wavelength of 274 nm and an emission wavelength of 464 nm, unless otherwise indicated. The retention times described herein were measured from time of injection to time of detection at the post-reactor unit fluorometer.

HPLC separation was performed on a 25 cm×4.6 mm X Terra MS C18 column (Waters; Milford, Mass.), 5 $\mu$m particle size, protected by a guard column. The system also included a C18 pre-column that was changed every 200 injections. Mobile phase A consisted of ammonium acetate (10 mM) at pH 6.50 with hydrogen peroxide (30% v/v) at a final concentration of 0.2%. Mobile phase B consisted of acetonitrile. The samples were eluted at a flow rate of 1 ml/minute, with a 20-minute linear gradient from 2 to 12.5% acetonitrile. After 20 minutes, the mobile phase was returned to 100% mobile phase A and re-equilibrated for 5 minutes. Samples were maintained at 4° C. and injected every 30 minutes with an autoinjector. The analytical column demonstrated no deterioration of its performance after up to 500 injections.

Methotrexate polyglutamate photolytic products were analyzed at an excitation wavelength of 274 nm and an emission wavelength of 464 nm. Spectral identification using the excitation spectra of the methotrexate polyglutamate post-column photolytic product in red blood cell extracts was performed by comparison with the excitation spectra of the methotrexate post-column photolytic product in water.

C. Calibration and Preparation of Standard Curves

Calibration and standard curves were performed essentially as follows. Standard curves were prepared by supplementing known amounts of purified $MTXPG_1$, $MTXPG_2$, $MTXPG_3$, $MTXPG_4$, $MTXPG_5$, $MTXPG_6$ and $MTXPG_7$ to a hemolysate prepared from a pool of red blood cells isolated from healthy donors (Blood bank; San Diego, Calif.). These "supplemented" red blood cell standards containing methotrexate polyglutamate concentrations ranging from 5 to 50 nmol/L packed red blood cells. Standard curves were fit by linear regression using peak area versus concentration.

D. Precision, Accuracy and Recovery

The precision, accuracy and recovery of the assays were determined as follows. Intra- and inter-day precision and accuracy were determined by analyzing low and high concentrations of methotrexate polyglutamates supplemented at known amounts into red blood cell hemolysates. Intra-day analysis was performed with 10 supplemented replicates, and inter-day evaluation was assessed with 5 replicates on 5 different days. Accuracy was calculated as the percentage error of the measured concentrations from the supplemented samples relative to the target concentration (measured concentration/target concentration×100%). Precision was determined by determining the coefficient of variation. Recoveries for methotrexate polyglutamates were determined by comparing the peak height from supplemented red blood cell samples with those from samples prepared with water at the same concentrations within the validated range.

E. Treatment of Patient Samples

Blood samples (5 ml) were collected from patients receiving low dose methotrexate therapy after written informed consent. Samples were centrifuged for 10 minutes to separate plasma and buffy coat from red blood cells. Red blood cells were washed with two volumes of saline and then stored at −70° C. until analysis.

A 100 µl aliquot of RBC hemolysate was briefly homogenized with 150 µl of water in an eppendorf tube before addition of 25 µl 70% perchloric acid to the mixture, vortexing for 10 seconds and centrifuging for 5 minutes. A total volume of 80 µl of red blood cell supernatant was directly injected onto the HPLC system.

Results were expressed as nmol/L packed red blood cells, and patient results were expressed as an average plus or minus the standard error of the mean (±SEM). Spectral identification of methotrexate polyglutamate post-column photolytic product was performed by comparison of the excitation spectra of post-column photolytic product of purified methotrexate in water.

EXAMPLE II

Quantification of Methotrexate Polyglumamate Concentration in Red Blood Cell Extracts by HPLC Fluorometry with Post-Column Derivatization This example describes determination of the intracellular concentration of methotrexate polyglutamates in patients treated with low-dose methotrexate therapy.

A. Separation and Detection of Methotrexate and Methotrexate Polyglutamates in Cellular Samples A chromatogram of a standard containing all seven methotrexate polyglutamates at a final concentration of 25 nmol/L each in water is presented in FIG. 2A. The retention times of individual methotrexate polyglutamates on the HPLC system described above were as follows: $MTXPG_7$: 12.5 minutes; $MTXPG_6$: 13.0 minutes; $MTXPG_5$: 13.7 minutes; $MTXPG_4$: 14.5 minutes; $MTXPG_3$: 15.7 minutes; $MTXPG_2$: 17.5 minutes; and $MTXPG_1$: 19.8 minutes. As shown in FIG. 2B in which the excitation spectra of $MTXPG_1$ through $MTXPG_7$ photolytic products are overlaid, the spectra of the different photolytic products are essentially identical. As further shown in FIG. 2B, the $MTXPG_1$ through $MTXPG_7$ photolytic products exhibited a maximum excitation wavelength at 274 nm.

Figure 3:
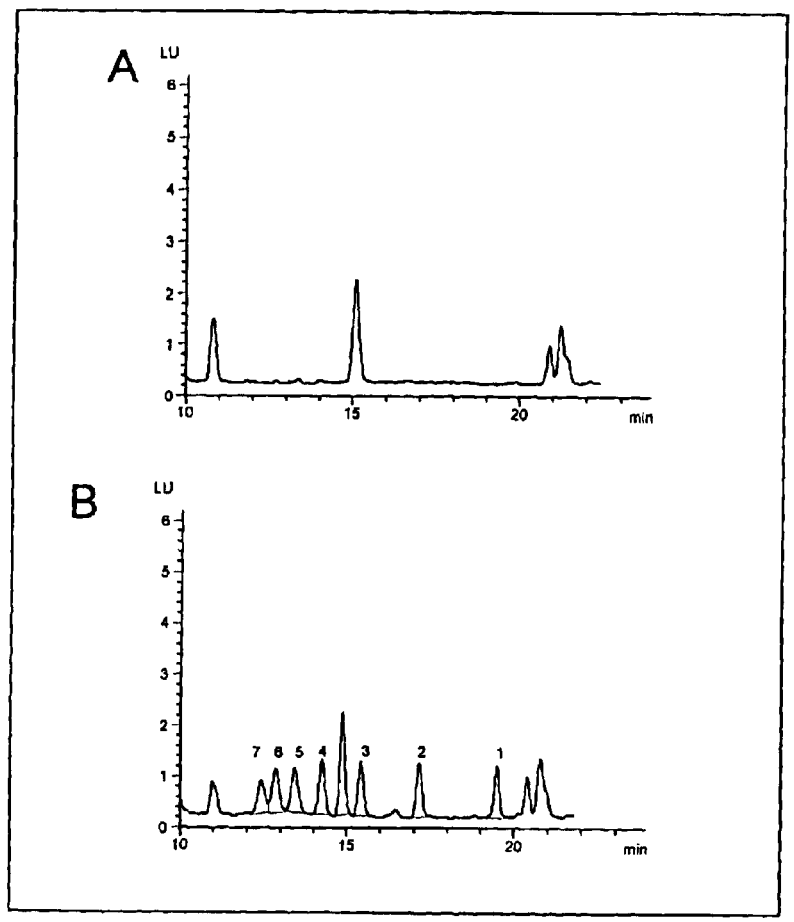
FIG. 3 shows chromatograms of control and supplemented red blood cell samples homogenized and treated with perchloric acid. The excitation wavelength was 274 nm, and the emission wavelength 464 nm. (A) Typical chromatogram of control red blood cell sample. (B) Typical chromatogram of a red blood cell sample supplemented with purified $MTXPG_1$ to $MTXPG_7$ at a final concentration of 25 nmol/L each. Equations describing the standard curves were: $MTXPG_1$, y=0.493x+0.245; $MTXPG_2$, y=0.540x+0.130; $MTXPG_3$, y=0.561x+0.125; $MTXPG_4$, y=0.568x+0.112; $MTXPG_5$, y=0.668x+0.01; $MTXPG_6$, y=0.710x+0.07; and $MTXPG_7$, y=0.430x+0.316, where y is the peak area and x is the supplemental concentration.

Typical chromatograms of control red blood cell extracts or red blood cell extracts supplemented with known amounts of purified methotrexate polyglutamates are shown in FIGS. 3A and B. Control (FIG. 3A) and supplemented (FIG. 3B) hemolysates were homogenized and perchloric acid treated as described above. Standard curves demonstrated a linear relationship between peak area and concentration, with correlation coefficients greater than 0.995 for all seven analytes.

Intra-day and inter-day precision and accuracy of the assay are summarized in Table I. The coefficients of variation for intra-day and inter-day precision were less than 15% at low and high concentrations of analytes. Accuracy ranged from 88 to 112% for the seven MTXPGs. Average extraction recoveries were as follows: 60% $MTXPG_1$; 66% $MTXPG_2$; 65% $MTXPG_3$; 66% $MTXPG_4$; 79% $MTXPG_5$; 80% $MTXPG_6$; and 60% $MTXPG_7$. The limits of detection, defined as three times the signal-to-noise ratio, were 2 nmol/L packed red blood cells. The limit of quantification for all seven methotrexate polyglutamates was 5 nmol/L packed red blood cells.

Figure 4:
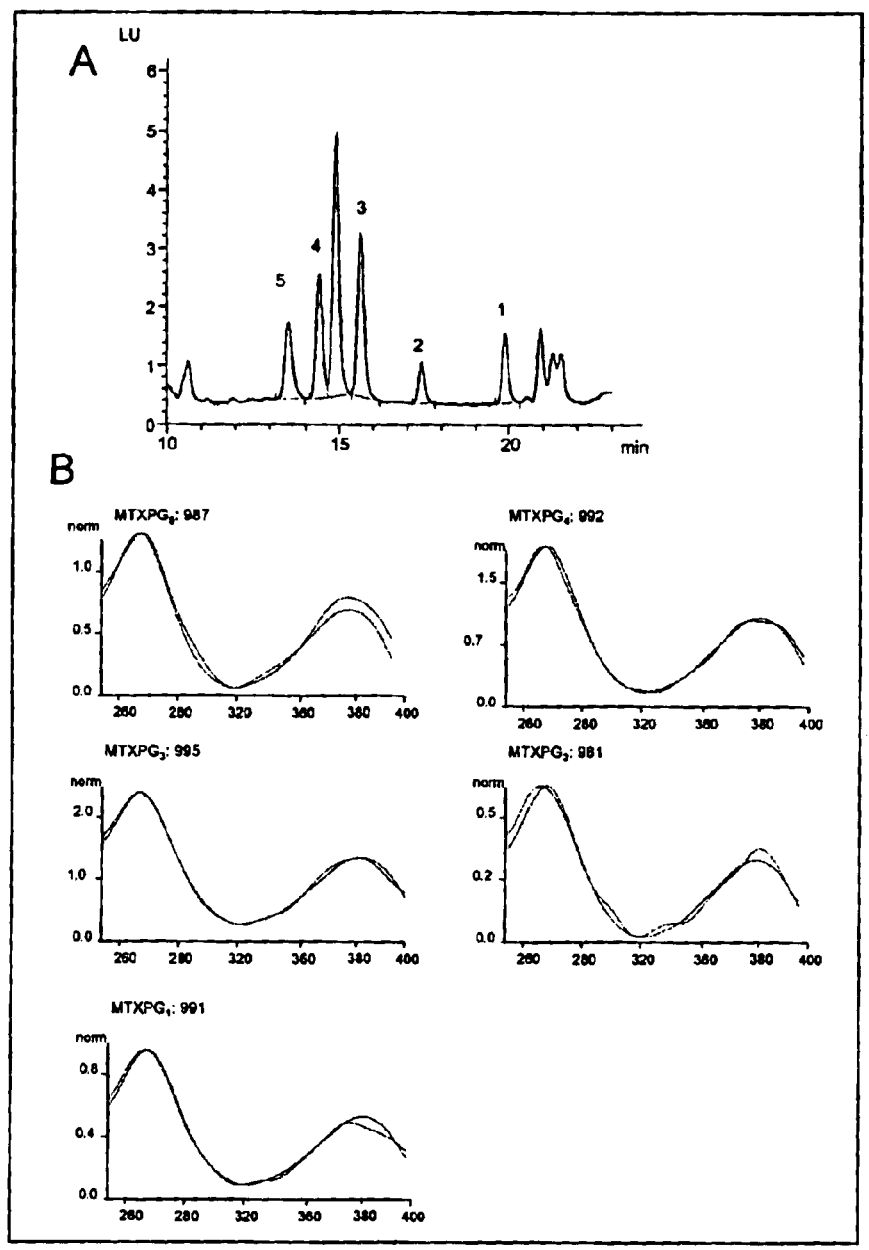
FIG. 4 shows the chromatogram of a red blood cell sample of a patient treated with low-dose methotrexate therapy. (A) Chromatogram of a patient on 17.5 mg weekly methotrexate for at least 3 months. Concentrations were as follows: 39 nmol/L $MTXPG_5$; 50 nmol/L $MTXPG_4$; 64 nmol/L $MTXPG_3$; 10 nmol/L $MTXPG_2$; and 27 nmol/L $MTXPG_1$. $MTXPG_6$ and $MTXPG_7$ were undetected in this sample. (B) Excitation spectra of each detected methotrexate polyglutamate photolytic product from the patient sample in A compared to the excitation spectra of the methotrexate photolytic product in water. The matching value was greater than 900 for each of the five spectral comparisons.

B. Detection of Methotrexate and Methotrexate Polyglutamates in Patient Red Blood Cell Samples Red blood cell samples were obtained from 14 patients with polyarthritis receiving low dose weekly methotrexate for at least three months. The weekly doses of methotrexate ranged from 10.0 to 25.0 mg with a median dose of 16.2 mg per week. FIG. 4A shows a typical patient chromatogram for a patient receiving 17.5 mg/week methotrexate. FIG. 4B shows that the excitation spectra of methotrexate polyglutamate photolytic products resolved from the patient sample was very similar to the spectra of the photolytic product of methotrexate in water.

Figure 5:
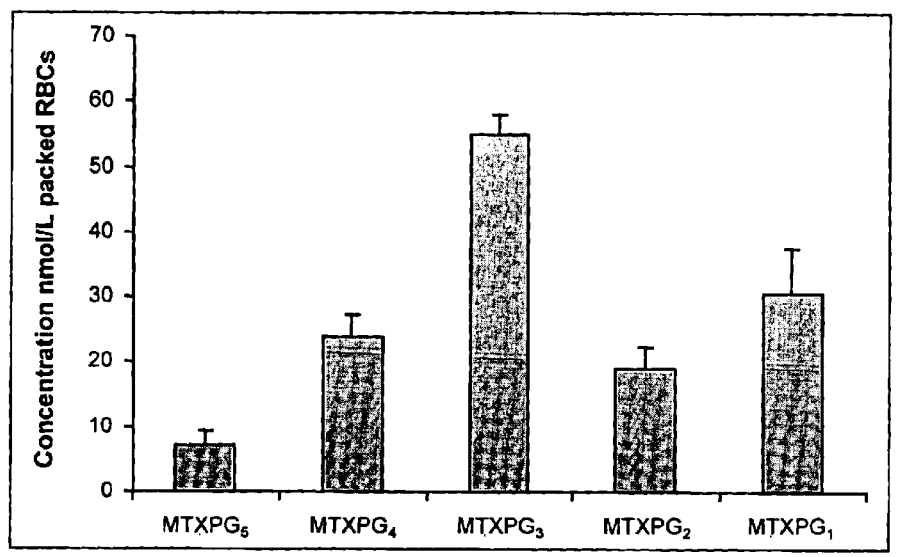
FIG. 5 shows average individual $MTXPG_1$ to $MTXPG_5$ concentrations in 14 patients with rheumatoid arthritis. $MTXPG_6$ and $MTXPG_7$ were undetected.

In the 14 patients receiving 10.0 to 25.0 mg/week methotrexate, the total methotrexate polyglutamate concentration ranged from 69 to 221 nmol/L RBC, with a median of 135 nmol/L RBC (see FIG. 5). $MTXPG_6$ and $MTXPG_7$ were undetected (<5 nmol/L) in all 14 patient samples, while $MTXPG_5$ was detected in 8 of 14 patient samples. The total average long chain polyglutamate concentration ($MTXPG_4$+ $MTXPG_5$) was 31±5.7 nmol/L and represented an average of 23% of total methotrexate polyglutamates. $MTXPG_3$ was the principal methotrexate polyglutamate detected in the patient samples, representing an average of 55% of total methotrexate polyglutamates.

Throughout this application various patent and non-patent publications have been referenced. The disclosures of these publications in their entireties are hereby incorporated by reference in this application in order to more fully describe the state of the art to which this invention pertains.

The term "comprising" as used herein is intended to be open-ended, including not only the recited elements, but further encompassing any additional elements.

Although the invention has been described with reference to the examples provided above, it should be understood that various modifications can be made without departing from the spirit of the invention. Accordingly, the invention is limited only by the claims.

We claim:

1. A method for determining a level of a methotrexate polyglutamate (MTXPG) in a red blood cell extract, comprising:

(a) resolving at least one MTXPG in a red blood cell extract obtained from a human undergoing methotrexate therapy; and (b) detecting at least one resolved MTXPG, thereby determining a level of said resolved MTXPG, wherein detection of said resolved MTXPG occurs without fractionation of said resolved MTXPG from other MTXPG species.

2. The method of claim 1, comprising determining a level of $MTXPG_3$, $MTXPG_4$ or $MTXPG_5$.

3. The method of claim 1, comprising determining a level of each of $MTXPG_1$ to $MTXPG_7$.

4. The method of claim 1, which can detect less than 500 nmol of each resolved MTXPG per liter packed red blood cells.

5. The method of claim 1, which can detect less than 50 nmol of each resolved MTXPG per liter packed red blood cells.

6. The method of claim 1, wherein said human has an autoimnume disease.

7. The method of claim 6, wherein said autoimmune disease is arthritis.

8. The method of claim 6 wherein said autoimmune disease is selected from the group consisting of rheumatoid arthritis, polyarthritis, systemic lupus erythematosus, and psoriasis.

9. The method of claim 1, wherein said human has cancer.

10. The method of claim 1, wherein step (a) comprises chromatography.

11. The method of claim 10 wherein said chromatography is high performance liquid chromatography (HPLC).

12. The method of claim 1, wherein step (b) comprises fluorimetry.

13. The method of claim 1, wherein step (b) comprises spectrophotometry.

14. The method of claim 1, wherein step (b) comprises mass spectrometry.

15. A method for determining a level of a methotrexate polyglutamate (MTXPG) in a red blood cell extract, comprising:

(a) resolving at least one MTXPG in the red blood cell extract, wherein said MTXPG contains no more than a natural abundance of radioactive isotopes; and (b) detecting at least one resolved MTXPG, thereby determining a level of said resolved MTXPG, wherein detection of said resolved MTXPG occurs without fractionation of said resolved MTXPG from other MTXPG species.

16. The method of claim 15, comprising determining a level of $MTXPG_3$, $MTXPG_4$ or $MTXPG_5$.

17. The method of claim 15, comprising determining a level of each of $MTXPG_1$ to $MTXPG_7$ and wherein detection of $MTXPG_1$ to $MTXPG_7$ does not require fractionation of the $MTXPG_1$ to $MTXPG_7$ species from each other.

18. The method of claim 15, wherein said red blood cell extract is obtained from a human.

19. The method of claim 15, which can detect less than 500 nmol of each resolved MTXPG per liter packed red blood cells.

20. The method of claim 15, which can detect less than 50 nmol of each resolved MTXPG per liter packed red blood cells.

21. The method of claim 15, wherein said red blood cell extract is from a human undergoing methotrexate therapy.

22. The method of claim 21, wherein said human has an autoimmune disease.

23. The method of claim 22, wherein said autoimmune disease is arthritis.

24. The method of claim 22, wherein said autoimmune disease is selected from the group consisting of rheumatoid arthritis, polyarthritis, systemic lupus erythematosus, and psoriasis.

25. The method of claim 21, wherein said human has cancer.

26. The method of claim 15, wherein step (a) comprises chromatography.

27. The method of claim 26, wherein said chromatography is high performance liquid chromatography (HPLC).

28. The method of claim 15 or 27, wherein step (b) comprises fluorimetry.

29. The method of claim 15 or 27, wherein step (b) comprises spectrophotometry.

30. The method of claim 15 or 27, wherein step (b) comprises mass spectrometry.

31. A method for determining a level of a methotrexate polyglutamate (MTXPG) in a red blood cell extract, comprising:

(a) resolving at least one MTXPG in the red blood cell extract;

(b) irradiating said at least one resolved MTXPG, thereby producing at least one resolved fluorescent MTXPG photolytic product; and (c) detecting said at least one resolved fluorescent MTXPG photolytic product, thereby determining a level of said MTXPG, wherein detection of said resolved fluorescent MTXPG photolytic product occurs without fractionation of said resolved fluorescent MTXPG photolytic product from other MTXPG species.

32. The method of claim 31, comprising determining a level of $MTXPG_3$, $MTXPG_4$ or $MTXPG_5$.

33. The method of claim 31, comprising determining a level of each of $MTXPG_1$ to $MTXPG_7$.

34. The method of claim 31, wherein step (b) comprises UV irradiating said at least one MTXPG.

35. The method of claim 34, wherein said UV irradiating utilizes radiation having a wavelength in the range of 225 nm to 275 nm.

36. The method of claim 35, wherein said UV irradiating utilizes radiation having a wavelength of 254 nm.

37. The method of claim 31, wherein step (a) comprises chromatography.

38. The method of claim 37, wherein said chromatography is high performance liquid chromatography (HPLC).

39. The method of claim 38, wherein step (b) is performed by irradiating said at least one MTXPG in a solvent having 0.05% to 1% $H_2O_2$.

40. The method of claim 39, wherein step (b) is performed by irradiating said at least one MTXPG in a solvent having 0.1% to 0.3% $H_2O_2$.

41. The method of claim 31, wherein step (b) comprises irradiating said at least one MTXPG for 0.5 to 60 seconds.

42. The method of claim 41, wherein step (b) comprises irradiating said at least one MTXPG for 0.5 to 15 seconds.

43. The method of claim 31, wherein step (c) comprises detecting fluorescence upon excitation in the range of 240 nm to 420 nm.

44. The method of claim 43, wherein step (c) comprises detecting fluorescence upon excitation in the range of 240 nm to 300 nm.

45. The method of claim 44, wherein step (c) comprises detecting fluorescence upon excitation with UV radiation at 274 nm.

46. The method of claim 43, wherein step (c) comprises detecting fluorescence upon excitation in the range of 360 nm to 410 nm.

47. The method of claim 31, wherein step (c) comprises detecting fluorescence at an emission wavelength in the range of 320 nm to 550 nm.

48. The method of claim 47, wherein step (c) comprises detecting fluorescence at an emission wavelength in the range of 440 nm to 500 nm.

49. The method of claim 48, wherein step (c) comprises detecting fluorescence at an emission wavelength of 464 nm.

50. The method of claim 49, wherein step (c) comprises detecting fluorescence upon excitation with UV radiation at 274 nm and at an emission wavelength of 464 nm.

51. The method of claim 31, wherein said red blood cell extract is obtained from a human.

52. The method of claim 31, which can detect less than 500 nmol of each resolved MTXPG per liter packed red blood cells.

53. The method of claim 31, which can detect less than 50 nmol of each resolved MTXPG per liter packed red blood cells.

54. The method of claim 31, wherein said red blood cell extract is from a human undergoing methotrexate therapy.

55. The method of claim 54, wherein said methotrexate is low-dose therapy.

56. The method of claim 54, wherein said human has an autoimmune disease.

57. The method of claim 56, wherein said autoimmune disease is arthritis.

58. The method of claim 56, wherein said autoimmune disease is selected from the group consisting of rheumatoid arthritis, polyarthritis, systemic lupus erythematosus, and psoriasis.

59. The method of claim 54, wherein said human has cancer.

60. A method of optimizing therapeutic efficacy or reducing toxicity associated with a predetermined methotrexate (MTX) dosage administered to a human, comprising:

(a) resolving at least one, methotrexate polyglutamate (MTXPG) in a red blood cell extract obtained from said human;

(b) detecting at least one resolved MTXPG, thereby determining a level of said resolved MTXPG; and (c) selecting a MTX dosage or a dose of folic acid or a derivative thereof to be subsequently administered to said human based on said level of resolved MTXPG, wherein detection of said resolved MTXPG occurs without fractionation of said resolved MTXPG from other MTXPG species.

61. The method of claim 60, comprising determining a level of $MTXPG_3$, $MTXPG_4$ or $MTXPG_5$.

62. The method of claim 60, comprising determining a level of each of $MTXPG_1$ to $MTXPG_7$.

63. The method of claim 60, wherein step (c) comprises altering said predetermined MTX dosage subsequently administered to said human.

64. The method of claim 63, wherein step (c) comprises reducing said predetermined MTX dosage subsequently administered to said human.

65. The method of claim 63, wherein step (c) comprises increasing said predetermined MTX dosage subsequently administered to said human.

66. The method of claim 60, wherein step (c) comprises altering a dose of folic acid, or a derivative thereof, subsequently administered to said human.

67. The method of claim 60, which can detect less than 500 nmol of each resolved MTXPG per liter packed red blood cells.

68. The method of claim 60, which can detect less than 50 nmol of each resolved MTXPG per liter packed red blood cells.

69. The method of claim 60, wherein said human has an autoimmune disease.

70. The method of claim 69, wherein said autoimmune disease is arthritis.

71. The method of claim 69, wherein said autoimmune disease is selected from the group consisting of rheumatoid arthritis, polyarthritis, systemic lupus erythematosus, and psoriasis.

72. The method of claim 60, wherein said human has cancer.

73. The method of claim 60, wherein step (a) comprises chromatography.

74. The method of claim 73, wherein said chromatography is HPLC.

75. The method of claim 60 or 74, wherein step (b) comprises fluorimetry.

76. The method of claim 60 or 74, wherein step (b) comprises spectrophotometry.

77. The method of claim 60 or 74, wherein step (b) comprises mass spectrometry.

* * * * *